US012496205B2

(12) United States Patent
Turconi et al.

(10) Patent No.: US 12,496,205 B2
(45) Date of Patent: Dec. 16, 2025

(54) KNEE BRACE FOR THE TREATMENT OF GONARTHROSIS

(71) Applicant: ORTHOSERVICE AG, Chiasso (CH)

(72) Inventors: Francesco Turconi, Monza (IT); Mauro Ravese, Villasanta (IT)

(73) Assignee: ORTHOSERVICE AG, Chiasso (CH)

(*) Notice: Subject to any disclaimer, the term of this patent is extended or adjusted under 35 U.S.C. 154(b) by 75 days.

(21) Appl. No.: 18/598,368

(22) Filed: Mar. 7, 2024

(65) Prior Publication Data

US 2024/0382332 A1 Nov. 21, 2024

(30) Foreign Application Priority Data

May 19, 2023 (IT) ........................ 102023000010188

(51) Int. Cl.
*A61F 5/01* (2006.01)

(52) U.S. Cl.
CPC .................................. *A61F 5/0109* (2013.01)

(58) Field of Classification Search
CPC .... A61F 5/0102; A61F 5/0104; A61F 5/0106; A61F 5/0123; A61F 5/0125; A61F 5/01; A61F 5/00; A61F 5/0109; A61F 5/0585; A61H 2001/0251; A61H 1/0262; A61H 1/0255; A61H 1/0237
See application file for complete search history.

(56) References Cited

U.S. PATENT DOCUMENTS

| | | | |
|---|---|---|---|
| 5,277,698 | A | 1/1994 | Taylor |
| 2018/0042749 | A1 | 2/2018 | Ingimundarson |
| 2019/0105188 | A1 | 4/2019 | Petursson |

FOREIGN PATENT DOCUMENTS

| | | | | |
|---|---|---|---|---|
| EP | 1830756 | A2 | 9/2007 | |
| EP | 3123986 | A1 * | 2/2017 | ........... A61F 5/0123 |

* cited by examiner

*Primary Examiner* — Ophelia A Hawthorne
(74) *Attorney, Agent, or Firm* — Dickinson Wright PLLC; Andrew D. Dorisio

(57) ABSTRACT

A knee brace for the treatment of gonarthrosis comprises a fabric base (11), an upper half-shell (12) and a lower half-shell (13), constrained to the fabric base (11), a rod (14), constrained to the two half-shells (12, 13), as well as a pressure element (17, 17') for laterally supporting the knee against the side opposite to the rod (14), at least one front belt (18', 18") and at least one rear belt (19', 19"), connected to the upper and lower half-shells (12, 13) and to the pressure element (17, 17'), wherein one or both of the upper or lower half-shells (12, 13) are provided with a traction device (20), comprising a lever (21) and an inextensible cord (22), which is constrained at one end to the lever (21) and at an opposite end to the front belt (18', 18") and passes through a front return slot (23) placed on the half-shell (12, 13).

12 Claims, 12 Drawing Sheets

KNEE BRACE FOR THE TREATMENT OF GONARTHROSIS

This application claims priority to Italian Patent Application No. 102023000010188 filed on May 19, 2023, the disclosure of which is incorporated by reference.

TECHNICAL FIELD

The present invention refers to a knee brace for the treatment of gonarthrosis.

BACKGROUND

Several different types of knee braces for the treatment of gonarthrosis, capable of transmitting specific forces to the knee, are known.

In the case of unicompartmental gonarthrosis, there is a thinning of the cartilage of the knee particularly on a side thereof, which causes pain due to the direct contact between the bone condyles of femur and tibia, especially when the knee is under load. Hereinafter, such side of the articulation will be referred to as “sick side” and the opposite side will be referred to as “healthy side”.

Knee braces acting on three push points, placed on opposite sides of the knee, so as to apply to the knee a load adapted to laterally “open” the sick side of the articulation subjected to cartilage deterioration, are known. The distribution of the push points on the knee provides that, on the healthy side of the articulation, there is a single push point substantially facing the articulation, while on the side of the knee wherein arthrosis appears, two push points are arranged, respectively placed above and below the articulation substantially at the same distance from the articulation.

The knee braces known, for example from U.S. Pat. No. 5,277,698 or EP 1 830 756 B1, comprise an upper half-shell and a lower half-shell joined by an articulated rod, adapted to be placed on the sick side of the knee, and one or more belts spirally wound between the two half-shells with both the ends applied on the side of the knee brace bearing the rod. Indeed, the single push point on the healthy side of the knee is determined by the contact point of the belts around the knee while the two opposite push points on the sick side of the knee are generated by the opposite ends of the articulated rod.

The main drawbacks of the known three-points knee braces mainly consist of wearability, which raises criticalities in wearing the knee brace, adjusting the same and tensioning the belts with a suitable tightening force.

The drawbacks with respect to wearability have an impact both on the comfort of the patient and on the effectiveness of the knee brace.

SUMMARY

An object of the present invention is to make a knee brace for the treatment of gonarthrosis which overcomes the drawbacks of the prior art.

Another object of the present invention is to make a knee brace for the treatment of gonarthrosis which achieves an optimal tensioning in use.

Another object of the present invention is to make a particularly simple and functional knee brace for the treatment of gonarthrosis, with low costs.

These objects according to the present invention are achieved by making a knee brace for the treatment of gonarthrosis.

Further features are provided in the dependent claims.

BRIEF DESCRIPTION OF DRAWINGS

The features and advantages of a knee brace for the treatment of gonarthrosis according to the present invention will be more apparent from the following exemplary and non-limiting description referred to the attached schematic drawings, in which.

DETAILED DESCRIPTION

Figure 1:
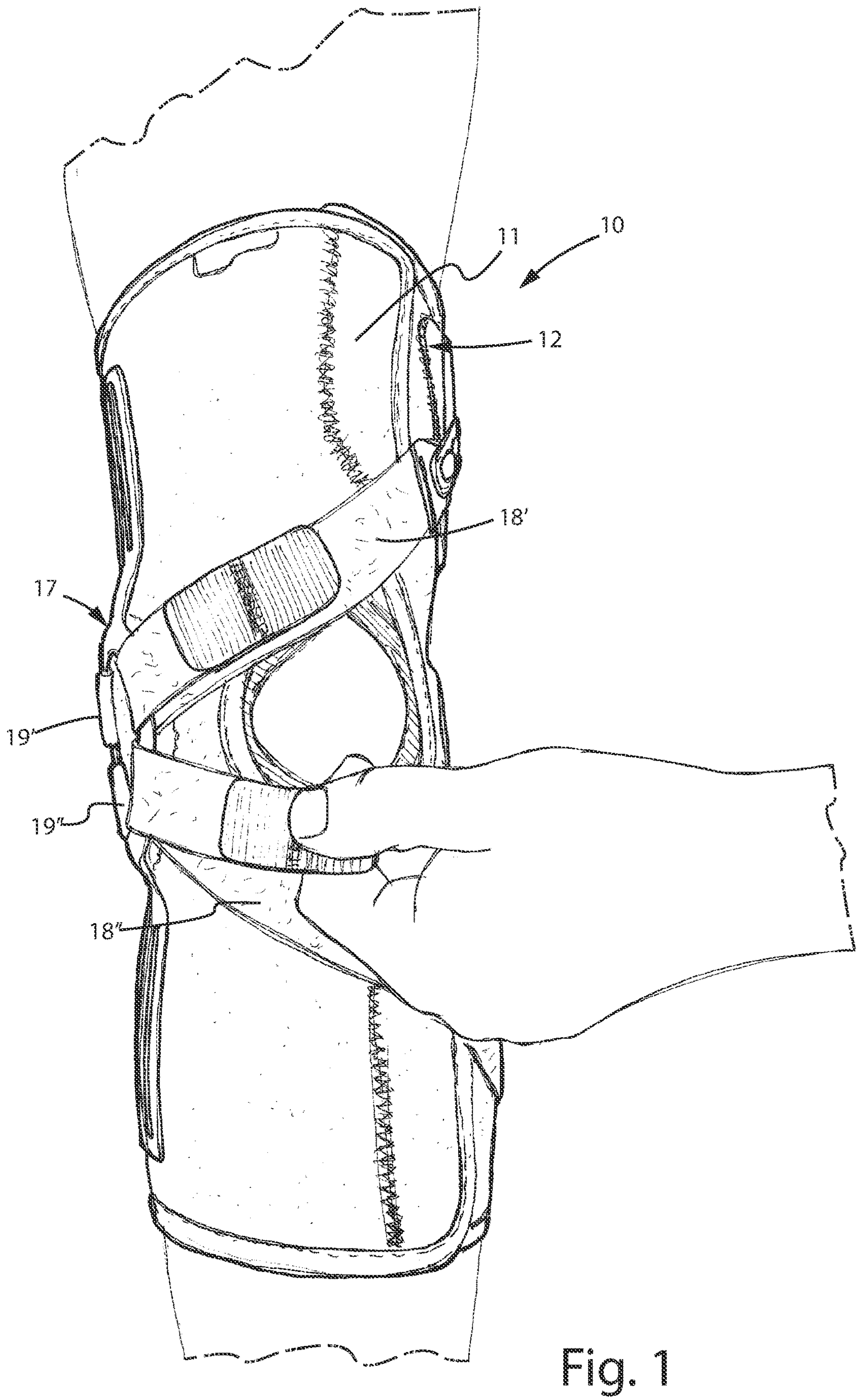
FIG. 1 is a front elevation view of the knee brace for the treatment of gonarthrosis according to a first embodiment of the present invention.
Figure 2:
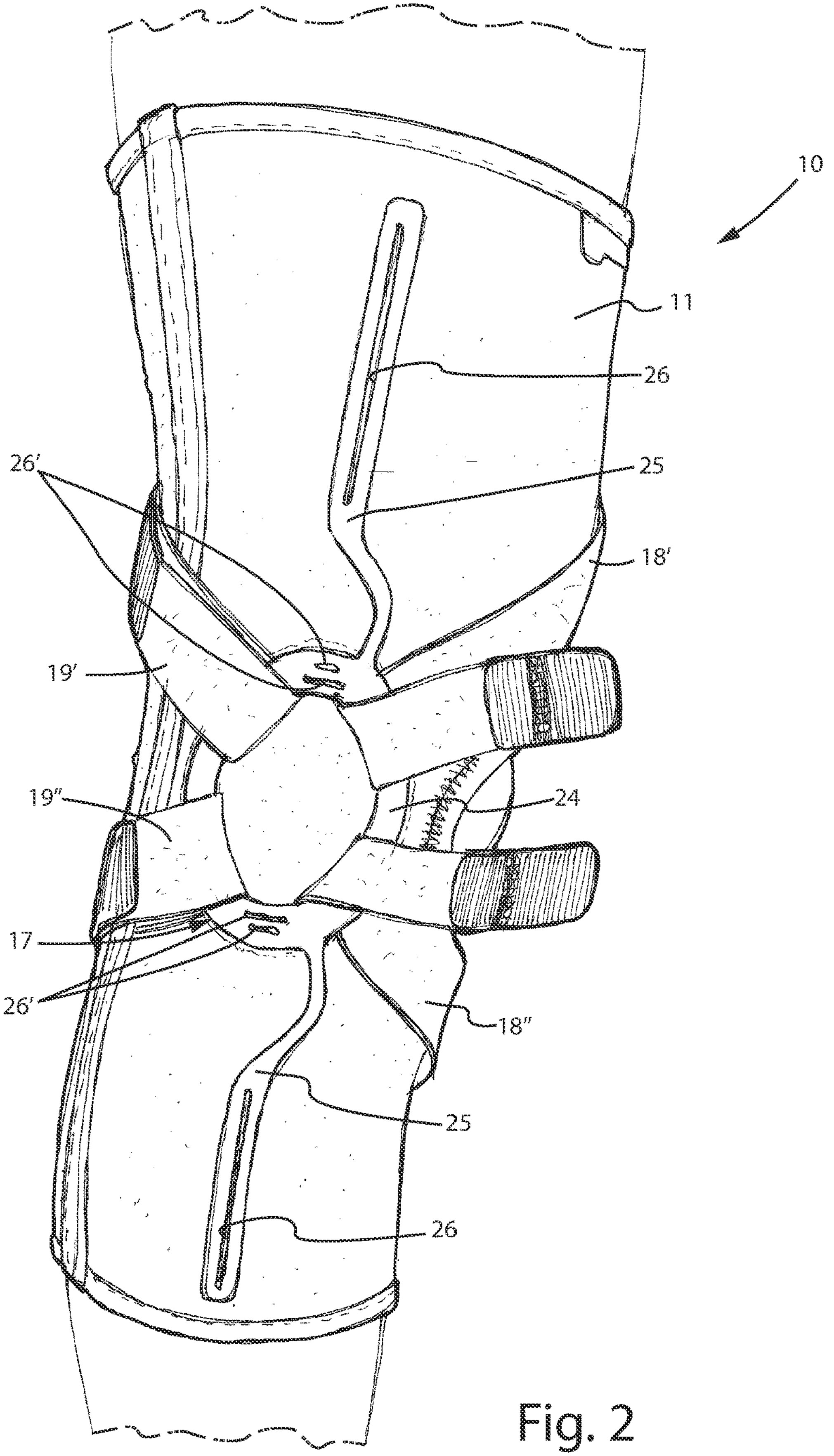
FIG. 2 is a side view of the knee brace of FIG. 1 which shows the pressure element placed on the healthy side of the knee, wherein the upper and lower front belts are open for adjusting in length.
Figure 3:
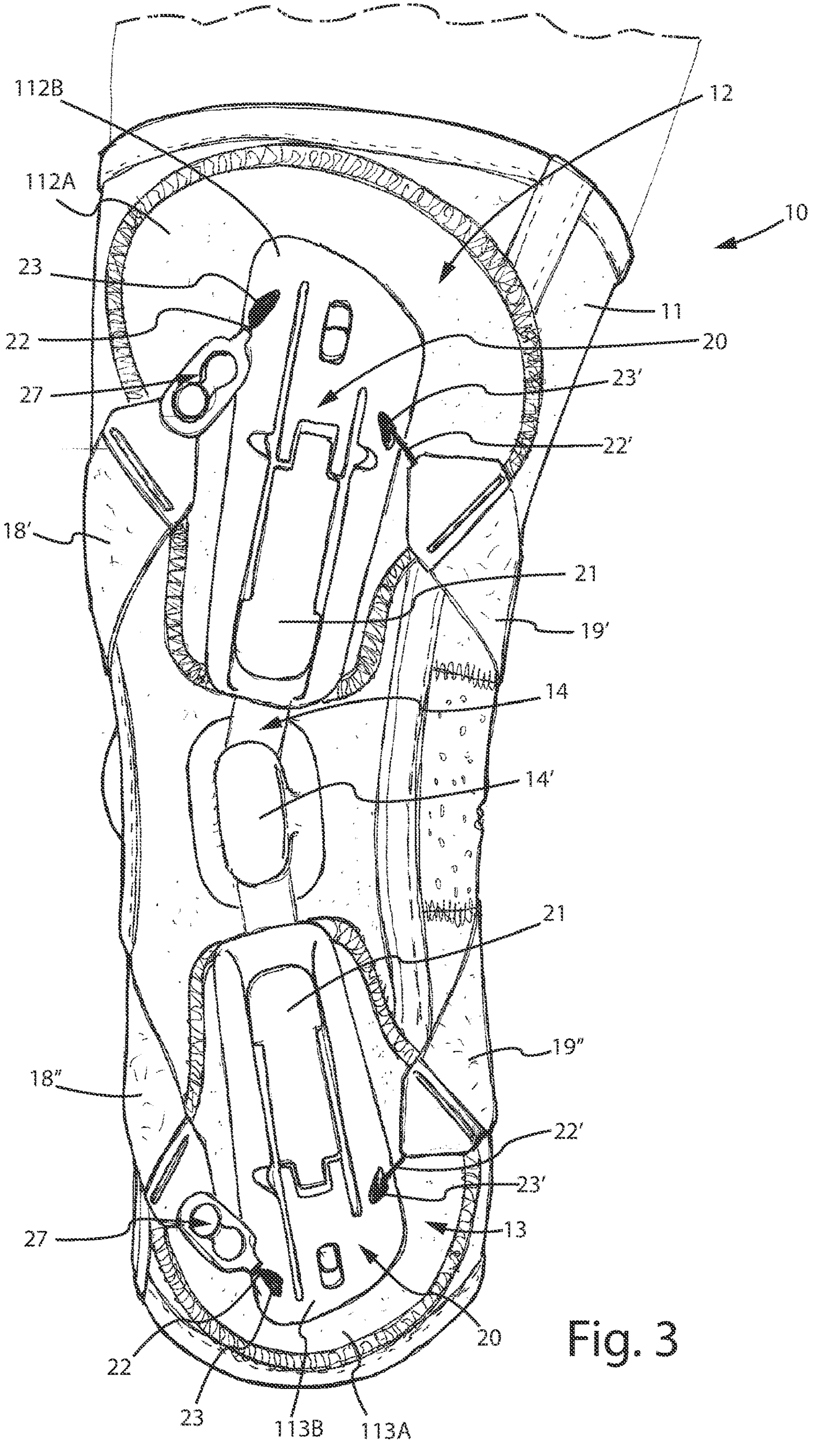
FIG. 3 is an opposite side view of the knee brace of FIG. 1 which shows the articulated rod placed on the sick side of the knee.
Figure 4:
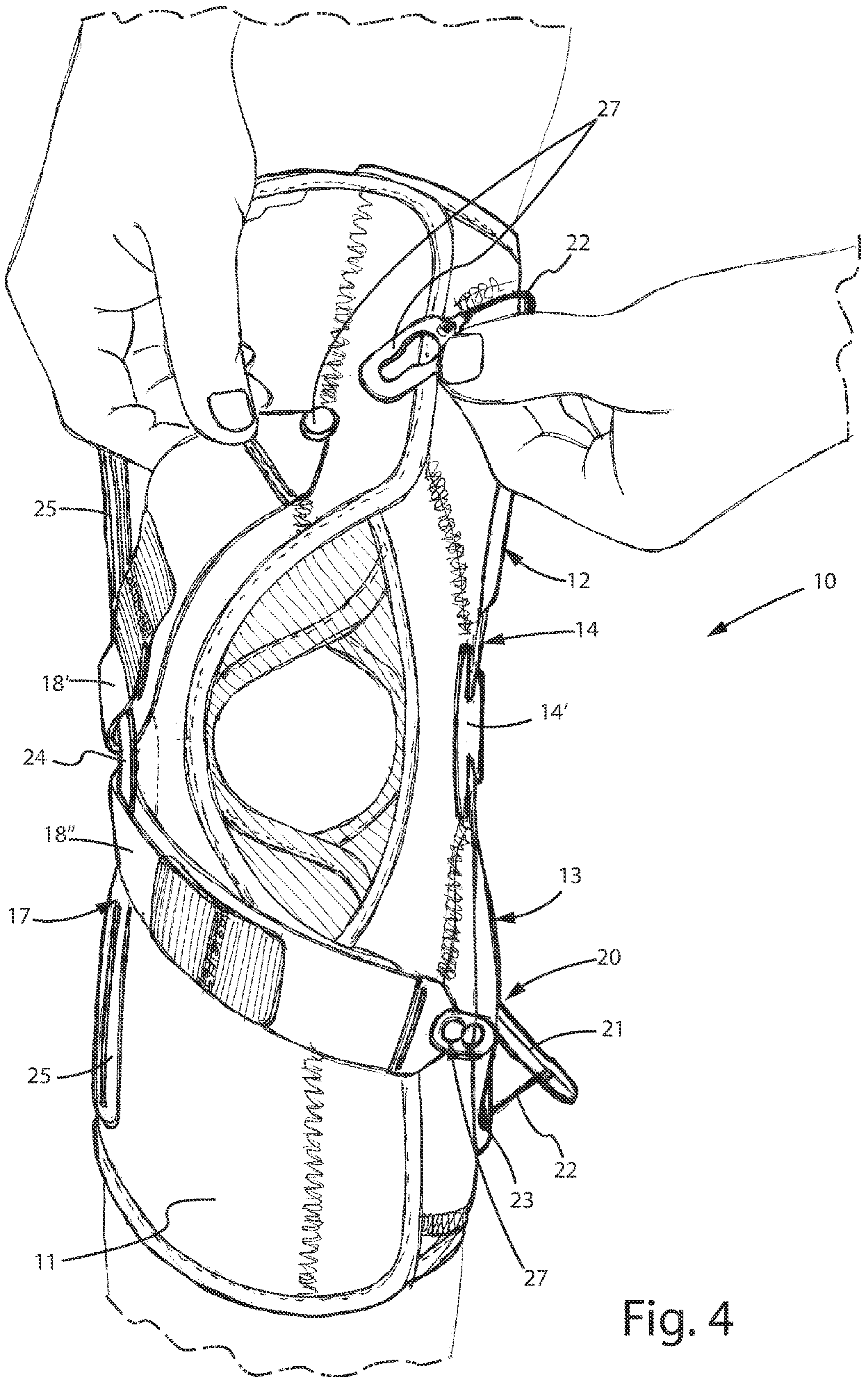
FIG. 4 shows the knee brace of FIG. 1 wherein the upper front belt is shown in the released position.
Figure 5:
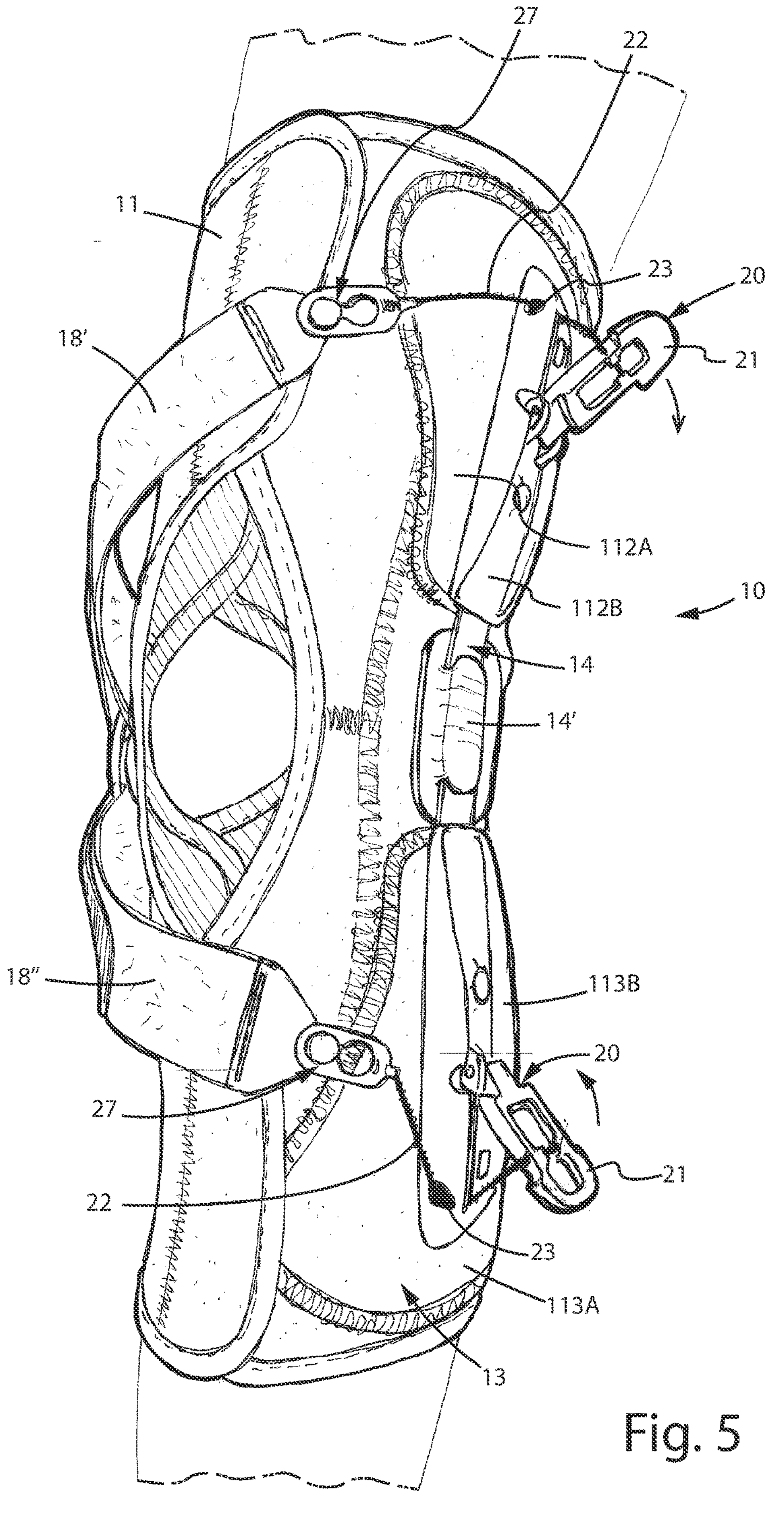
FIG. 5 shows the knee brace of FIG. 1 wherein the upper and lower front belts are engaged, and the respective levers are open.

With reference to the figures, a knee brace for the treatment of gonarthrosis overall indicated by 10 is shown, comprising a fabric base 11, an upper half-shell 12, a lower half-shell 13, both constrained to the fabric base 11, and a pressure element 17, 17' for laterally supporting a knee.

The knee brace 10 is provided with a traction belt system, comprising at least one front belt 18', 18" and at least one rear belt 19', 19", connected to the upper and lower half-shells 12, 13 and to the pressure element 17, 17'.

All the belts are adjustable in length, preferably by quick-engagement means of the hook-and-loop type (Velcro©).

According to the first embodiment shown in FIGS. 1 to 5, the knee brace 10 comprises an upper front belt portion 18' and a lower front belt portion 18", each constrained to opposite ends to the related upper 12 or lower 13 half-shell and to the pressure element 17, as well as an upper rear belt portion 19' and a lower rear belt portion 19", each constrained to opposite ends to the related upper 12 or lower 13 half-shell and to the pressure element 17.

Figure 6:
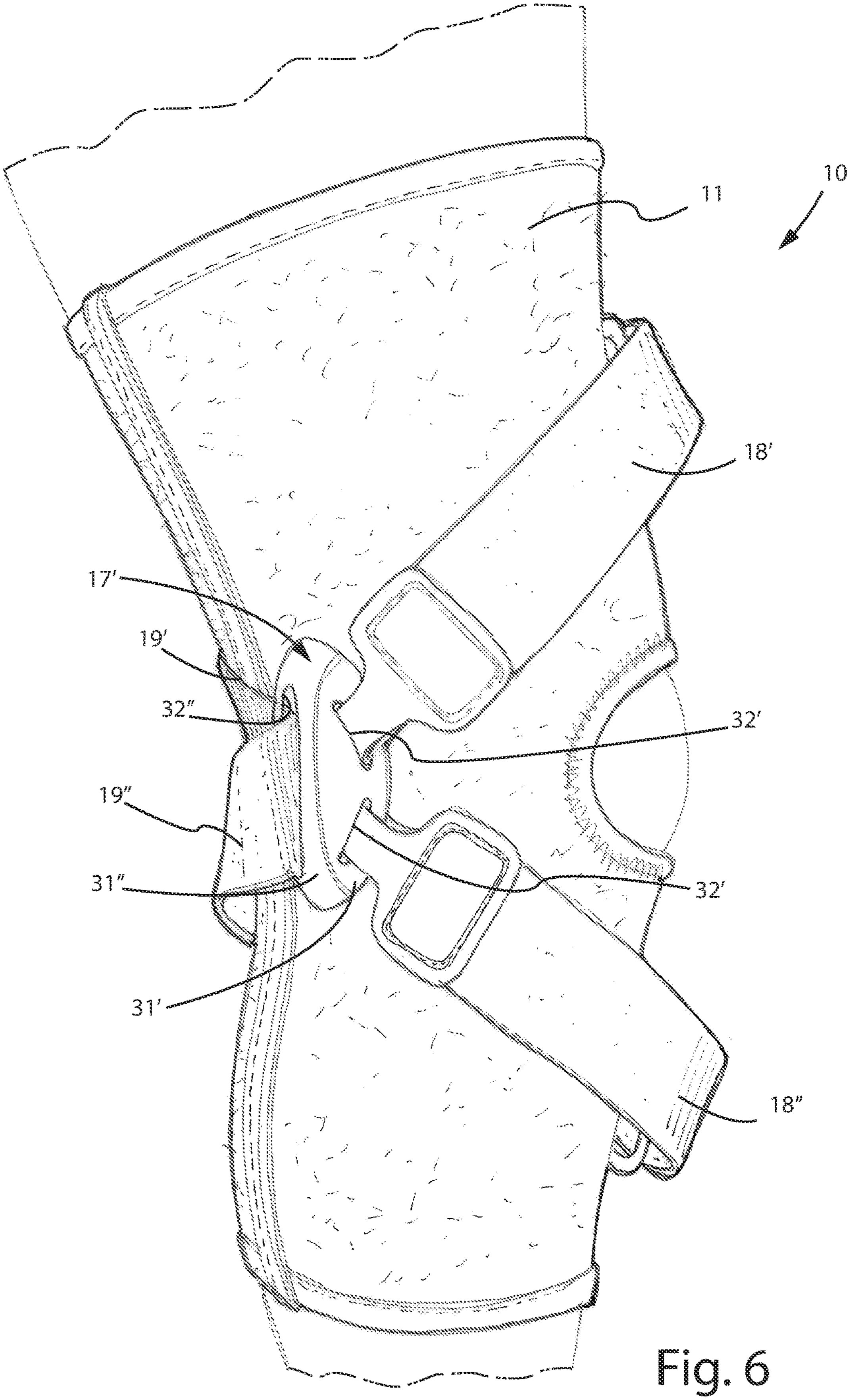
FIG. 6 shows a knee brace for the treatment of gonarthrosis according to a second embodiment of the present invention, wherein the pressure element is openable.
Figure 7:
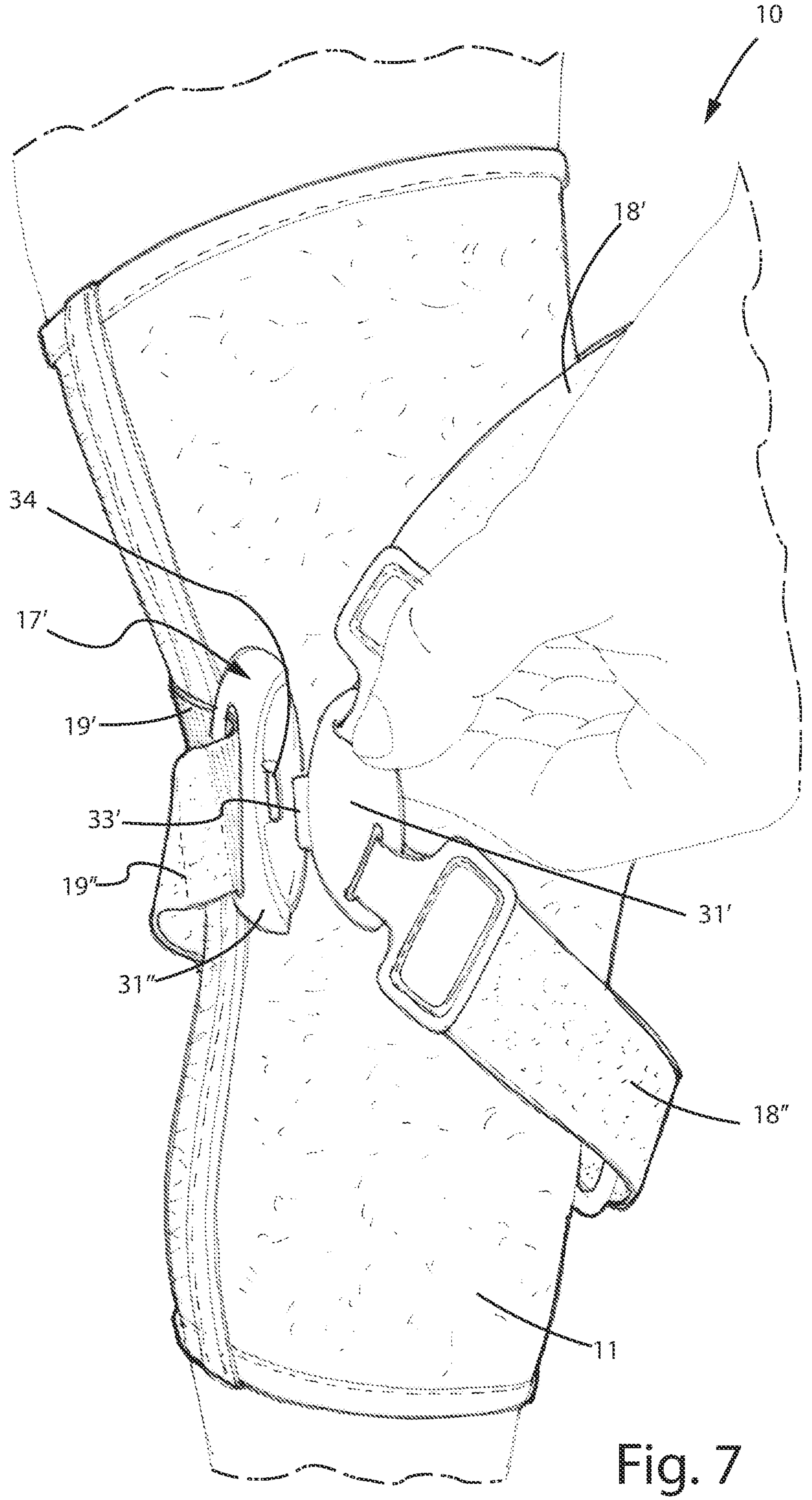
FIG. 7 shows the knee brace of FIG. 6 wherein the pressure element is shown in the open position.
Figure 8:
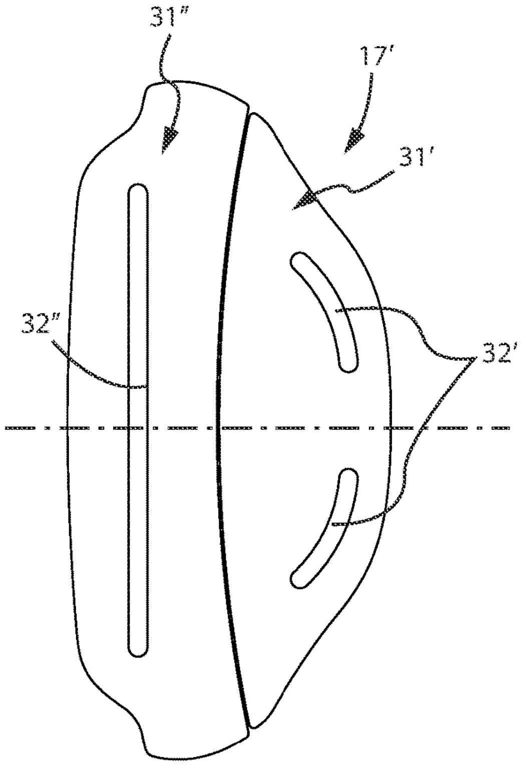
FIGS. 8 and 9 are a plan view and a cross section of the openable pressure element placed in the closed position, respectively.
Figure 10:
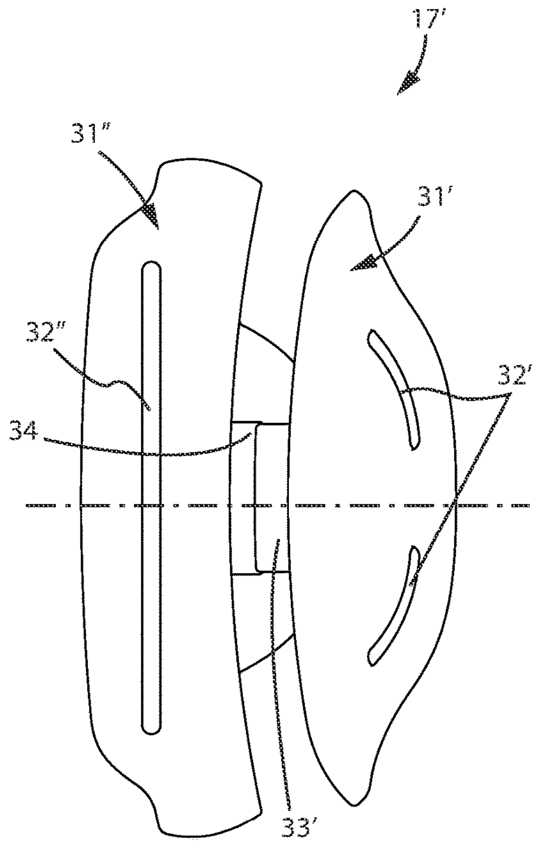
FIGS. 10 and 11 are a plan view and a cross section of the openable pressure element placed in the open position, respectively.
Figure 9:
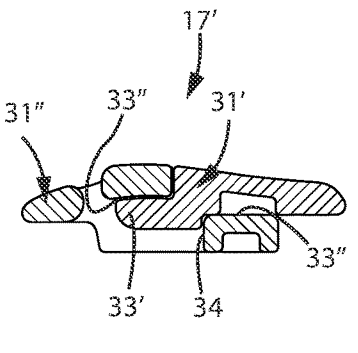
Figure 11:
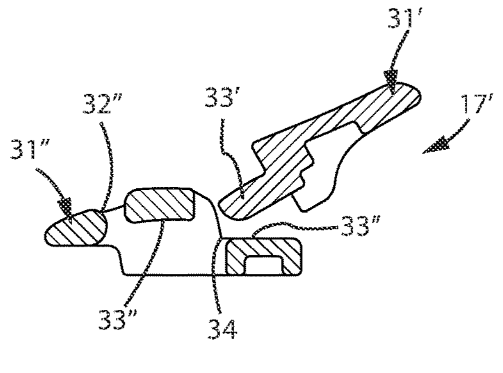
Figure 12:
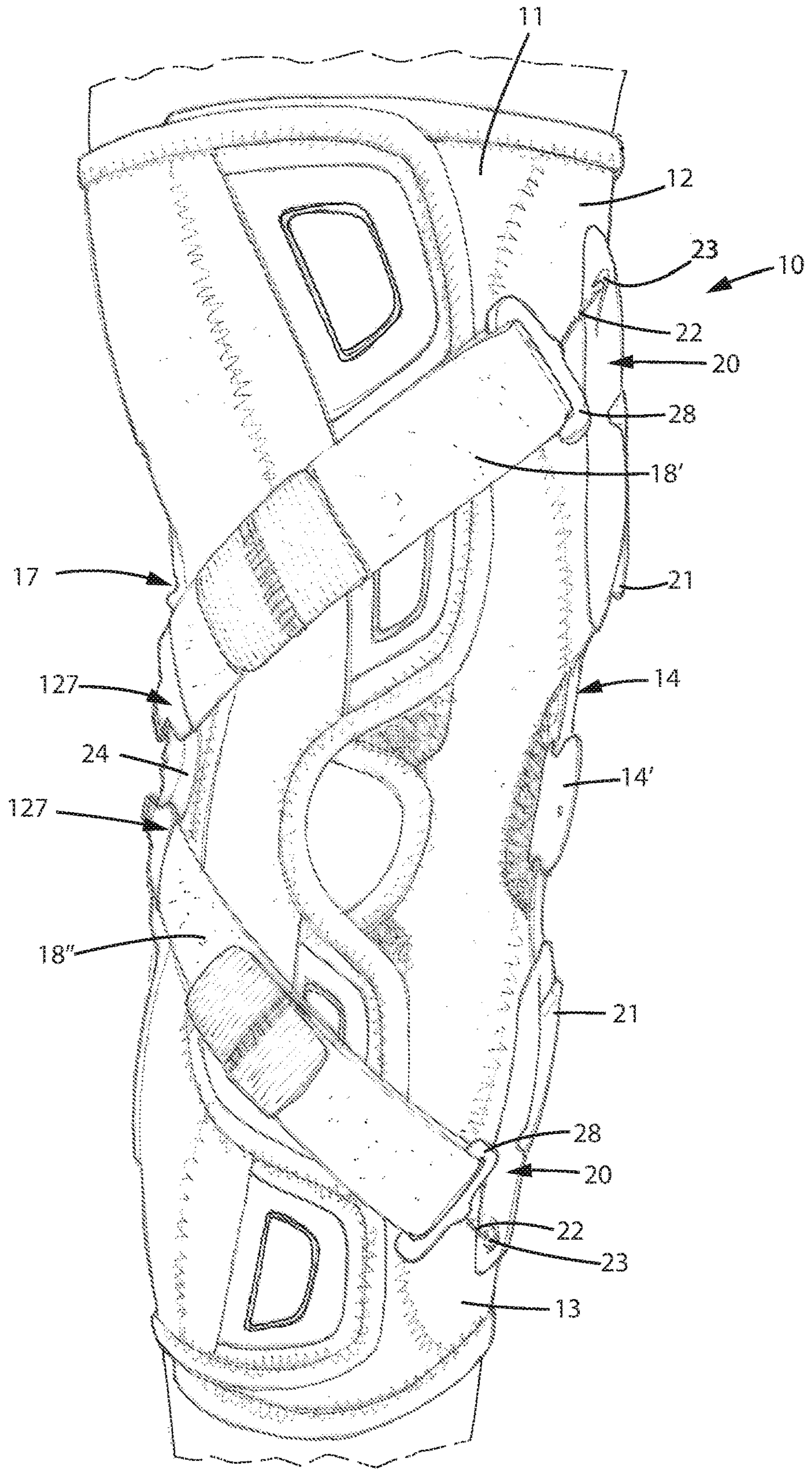
FIGS. 12 to 15 show a knee brace for the treatment of gonarthrosis according to a further embodiment of the present invention.
Figure 13:
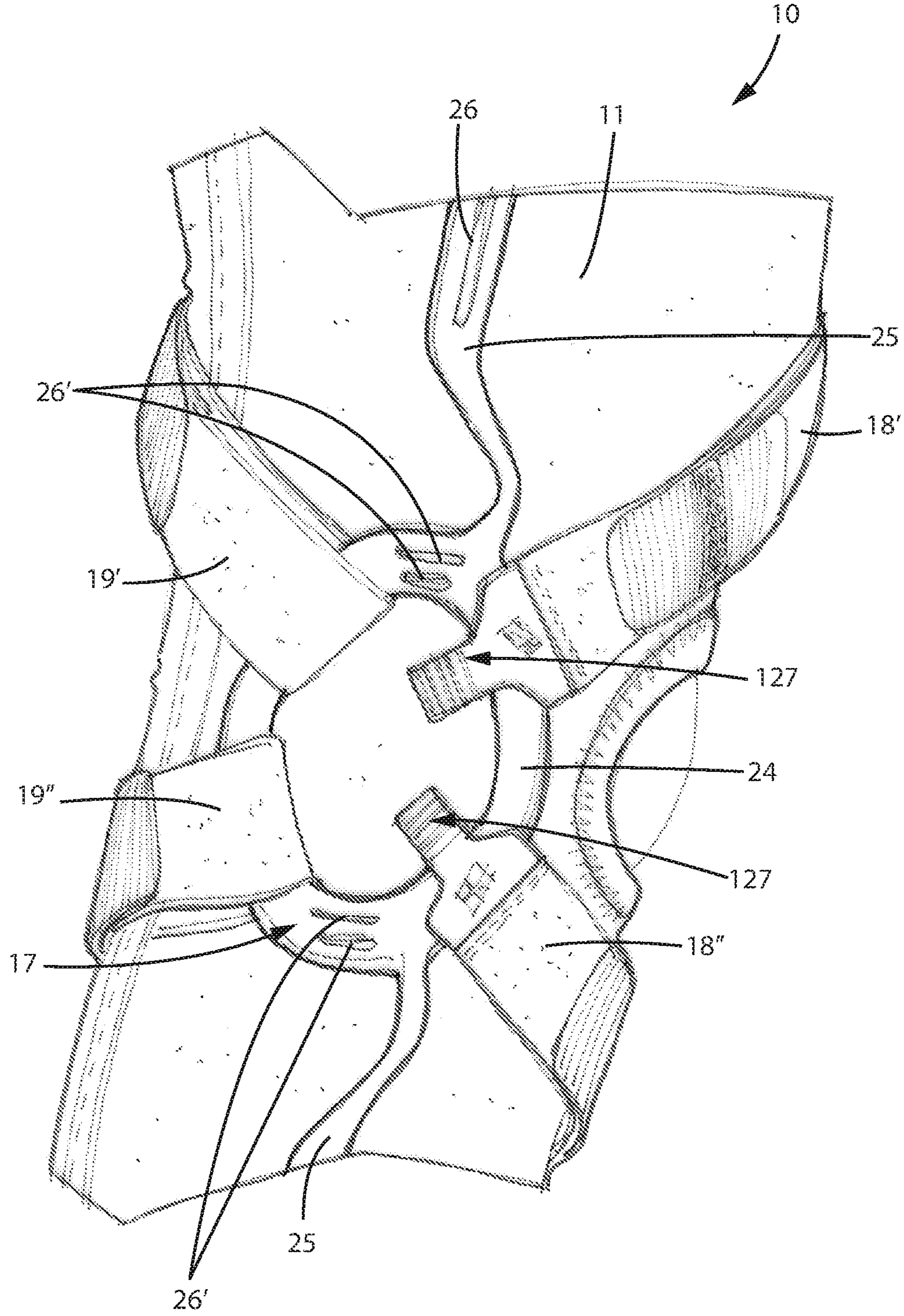
Figure 14:
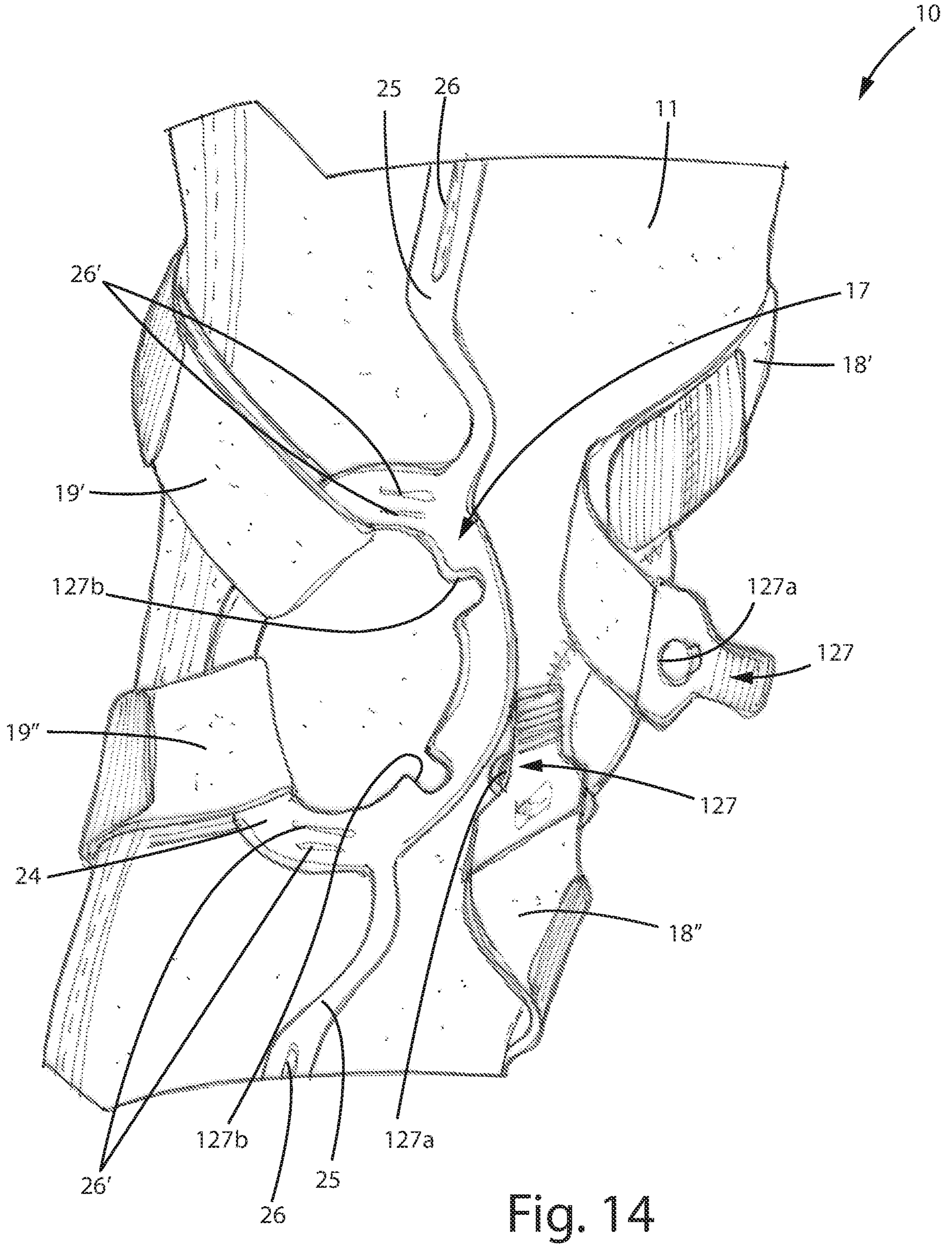
Figure 15:
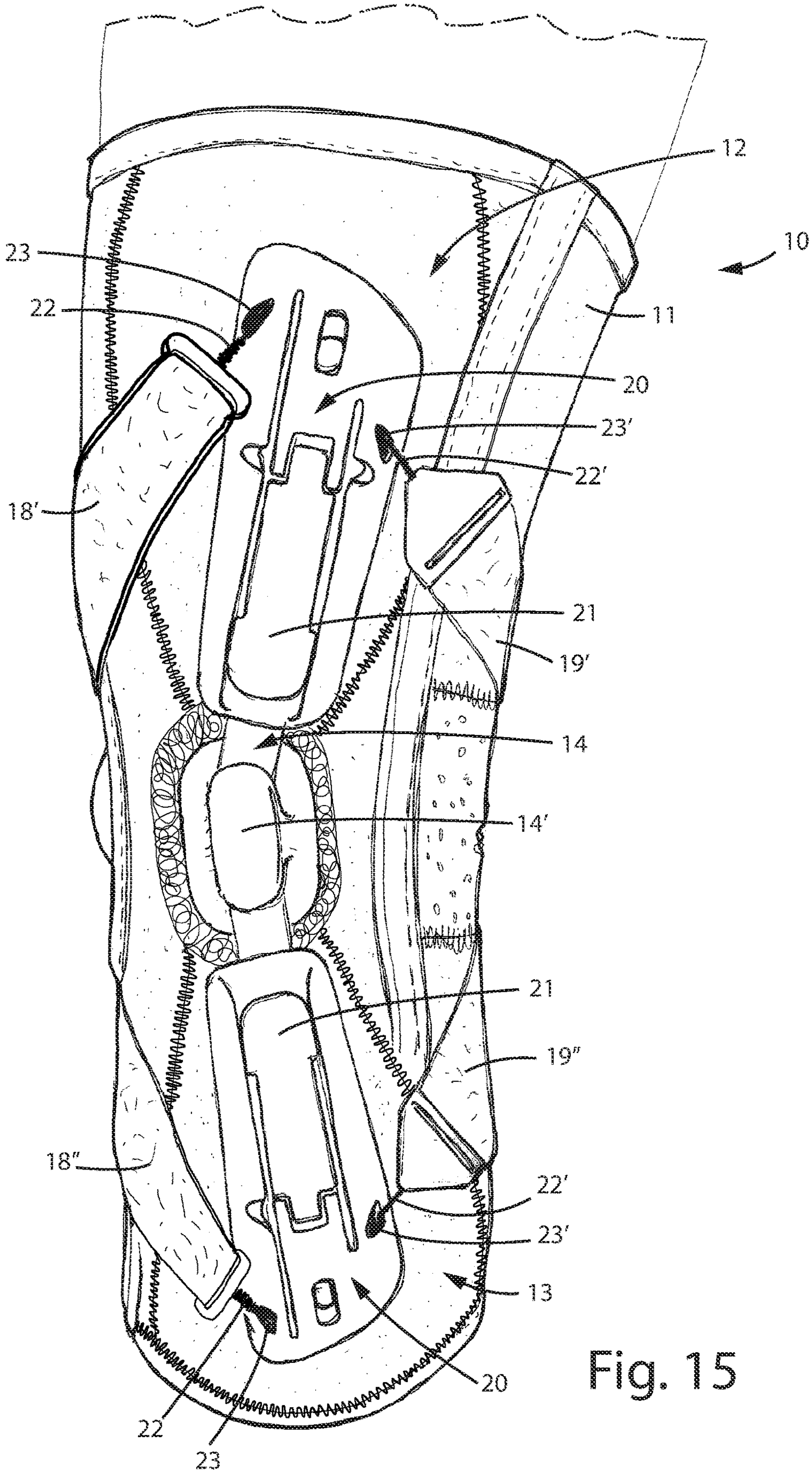

In the second embodiment of the knee brace 10, shown in FIGS. 6 and 7, the upper rear belt portion 19' and the lower rear belt portion 19" are joined together to form a single rear belt returned in the pressure element 17'.

According to the invention, the knee brace 10 further comprises a rod 14, constrained to the two half-shells 12 and

13, preferably removably, adapted to be placed laterally on the sick side of the knee which should be relieved of the load, opposite to the pressure element 17, 17'.

The rod 14, shown in the figures, is an articulated rod provided with a central joint, coinciding with an articulation point 14' of the knee brace, but it could be replaced by a flexible stick or other equivalent means, still capable of bending in the articulation point 14' of the knee brace. The object of the articulated rod 14 is substantially to keep the knee brace 10 stretched when the front 18 and rear 19 belts are placed in traction in operation and create a force which would tend to move the upper and lower ends of the brace closer.

The rod 14 could be inserted in a pocket inside the fabric base 11 or be constrained in a position external thereto, as shown in the figures.

According to the invention, the knee brace 10 comprises a traction device 20 placed on one of the upper 12 or lower 13 half-shells or a traction device 20 placed on each of the half-shells 12, 13 as shown in the figures.

The traction device 20 comprises a lever 21 and an inextensible cord 22, which is constrained at a first end to the lever 21 and at an opposite end to the front belt 18', 18" and passes through a front return slot 23, placed on the upper 12 or lower 13 half-shell.

Advantageously, according to a shown preferred embodiment, the traction device 20 comprises a second inextensible cord 22', which is constrained at a first end to the same lever 21 and at an opposite end to the rear belt 19', 19" and passes through a rear return slot 23' placed on the upper 12 or lower 13 half-shell.

Preferably, both the upper half-shell 12 and the lower half-shell 13 of the knee brace 10 bear the described traction device 20.

Preferably, in the traction device 20 the distance between the articulation point 14' of the knee brace 10 and the front return slot 23 is greater than the distance between the articulation point 14' and the rear return slot 23'. Indeed, arranging the front return slots 23 more spaced apart from each other along the height of the knee brace 10 than the rear return slots 23' advantageously contrasts the tendency of the rod 14 to remain permanently flexed.

The half-shells 12, 13 preferably consist of two plastic parts, a flexible portion 112A, 113A, possibly covered with fabric and constrained, for example by stitching, to the fabric base 11, and a rigid plate 112B and 113B, bearing the traction device 20.

In both the half-shells 12, 13 the rigid plate 112B, 113B is removably fastened to the ends of the rod 14.

Preferably, the rigid plates 112B and 113B of the half-shells 12, 13 bear the front 23 and rear 23' return slots.

According to the first embodiment of the invention, the pressure element 17 comprises a ring 24, to which all the front and rear belts 18', 18", 19', 19" converge, and two stabilizing rods 25, placed above and below the ring 24 to stiffen the side portion of the fabric base 11 and preferably facilitate, by the presence of seats 26, the constraint by stitching the pressure element 17 to the fabric base 11.

There can also be further seats 26' along the ring 24 still for the constraint by stitching of the pressure element 17 with the fabric base 11.

According to the invention, at least one front belt 18', 18" of the knee brace 10 is provided at one of its ends with a quick-release device 27, 127.

Preferably, according to the first embodiment shown in FIGS. 1 to 5, on the front side of the knee brace 10 the constraint between the first and the second inextensible cords 22 and the upper front belt 18' and the lower front belt 18", respectively, is of the releasable type, through the front quick-release device 27 in order to open the knee brace 10 at the front and wound it around the leg.

According to a further embodiment of the knee brace 10 for the treatment of gonarthrosis according to the present invention, shown in FIGS. 12 to 15, the quick-release device 127 is placed between the upper front belt 18' and the lower front belt 18", respectively, and the ring 24 of the pressure element 17.

The quick-release device 127 comprises, in the example shown for exemplary and non-limiting purposes, a protruding knob 127*a*, made at the free end of the upper front belt 18' and the lower front belt 18", adapted to engage with its own seat 127*b* made on the ring 24.

With the only exception being the arrangement of the quick-release devices 127, which are placed between the upper 18' and lower 18" front belts and the ring 24 of the pressure element 17, for all the remaining details, the knee brace 10 according to the further embodiment of the invention identically recalls what is described for the first embodiment of FIGS. 1-5 to which reference is integrally made.

In the front part of the knee brace 10 according to the invention shown in FIGS. 12-15 the upper front belt 18' and the lower front belt 18" are connected to the first and the second inextensible cords 22 each by a front slot 28, within which they are returned.

The arrangement of the quick-release devices 127 on the ring 24 advantageously allows to engage and release the belts using only one hand.

According to the second embodiment of the knee brace 10 shown in FIGS. 6 to 10, the pressure element 17' is of the openable type, in order to allow to make the knee brace 10 openable at the front by a simple movement and to simultaneously close all the belts 18', 18", 19', 19".

The openable pressure element 17' comprises two complementary engaging portions 31', 31" engageable to and separable from each other, each bearing slots 32', 32" for fastening the front and rear belts, respectively.

A first engaging portion 31' bears a tooth 33' adapted to be diagonally inserted into an opening 34 of the opposite second engaging portion 31" and to be in abutment, on opposite faces thereof, against complementary portions 33" of the second engaging portion 31".

The openable pressure element 17' provides in operation an appropriate safety with respect to the risk of accidental opening because the traction of the belts on the same occurs in the plane of the element itself or in the bandaging direction of the knee, while the movement required to open it is opposite, that is requires that the engaging portion 31' bearing the tooth 33' is raised upwards and then moved away from the knee. The engaging portion 31" is preferably fastened to the fabric base 11 in order to maintain a stable position and simplify the operations to wear the knee brace.

In the knee brace 10 according to the invention, the fabric base 11 can be indifferently made open at the front to be easily worn without being inserted from the foot, according to a first embodiment, or closed, as a tubular element, according to a further embodiment.

The constructive elements described for the different embodiments are equivalently interchangeable with each other.

The knee brace 10 according to the invention, when firstly applied on a patient, provides the adjustment of the length of the front adjusting belts 18, comprising the upper front belt 18' and the lower front belt 18", and the rear ones 19, comprising the upper rear belt 19' and the lower rear belt 19" by action on the Velcro @ adjustment.

After the first application of the knee brace 10, and for all the subsequent applications, the knee brace 10 is tightened by the lever traction devices 20, which put the belts 18 and 19 in traction.

In order to open and wear the knee brace without modifying the adjustments of the lengths of the belts, the quick-release devices 27 placed between the upper 18' and lower 18" front belts and the traction device 20, the quick-release devices 127 placed between the upper 18' and lower 18" front belts and the pressure element 17 are used, or an action can be exerted on the complementary engaging portions 31', 31" engageable to and separable from each other integrated in the openable pressure element 17'.

The system of belts, converging to the centre of the knee, on the side opposite to the rod, creates a push point which, together with the two push points at the upper and lower ends of the rod, assists in supporting the knee affected by unicompartmental gonarthrosis and in alleviating the pain created by "rubbing" the compartment affected by arthrosis.

The support is medio-lateral or latero-medial depending on using a right or left knee brace on the right or left knee.

The knee brace for the treatment of gonarthrosis being the object of the present invention has the advantage of allowing the user to quickly close the same, with little force and always alike, i.e., with a repeatable traction application.

Furthermore, advantageously each lever preferentially applies tension both at the front and at the rear simultaneously.

In the knee brace for the treatment of gonarthrosis according to the invention, the used materials, as well as the size, can be any depending on the technical requirements.

The invention claimed is:

1. A knee brace for the treatment of gonarthrosis comprising a fabric base, an upper half-shell and a lower half-shell, constrained to the fabric base, a rod, constrained to the two half-shells, as well as a pressure element for laterally supporting the knee against the side opposite to said rod, at least one front belt and at least one rear belt, connected to said upper and lower half shells and to said pressure element, wherein one of the upper or lower half-shells or both the upper and lower half-shells are provided with a traction device comprising a lever and an inextensible cord, which is constrained at one end to the lever and at an opposite end to the at least one front belt and passes through a front return slot placed on the half-shell.

2. The knee brace according to claim 1, wherein the at least one front belt is provided with a quick-release device at one end of the at least one front belt.

3. The knee brace according to claim 2, wherein the quick-release device is placed at the front for the constraint between the inextensible cord and the at least one front belt.

4. The knee brace according to claim 2, wherein said quick-release device-is placed between the at least one front belt and the pressure element.

5. The knee brace according to claim 1, wherein the traction device comprises a second inextensible cord, which is constrained at one end to the lever and at an opposite end to the rear belt and passes through a rear return slot placed on the half-shell.

6. The knee brace according to claim 5, wherein a distance between an articulation point of the knee brace and the front return slot is greater than a distance between the articulation point and the rear return slot.

7. The knee brace according to claim 1, wherein the at least one front belt comprises an upper front belt portion and a lower front belt portion, and the at least one rear belt comprises an upper rear belt portion and a lower rear belt portion.

8. The knee brace according to claim 7, wherein said upper rear belt portion and said lower rear belt portion are joined together and returned in a slot or ring of the pressure element.

9. The knee brace according to claim 1, wherein the pressure element is openable and comprises two complementary engaging portions engageable to and separable from each other, each bearing slots for fastening the belts.

10. The knee brace according to claim 9, wherein a first engaging portion-bears a tooth-adapted to be diagonally inserted into an opening of an opposite second engaging portion and being in abutment against complementary portions of the second engaging portion.

11. The knee brace according to claim 1, wherein the belts are adjustable in length.

12. The knee brace according to claim 1, wherein the half-shells comprise a flexible portion and a rigid plate, bearing the traction device.

* * * * *